United States Patent [19]

Haas et al.

[11] Patent Number: 4,874,797

[45] Date of Patent: Oct. 17, 1989

[54] OLIGOUREA POLYOLS, POLYETHER POLYOLS PRODUCED FROM THEM AND THE USE OF THESE POLYOLS IN THE ISOCYANATE POLYADDITION PROCESS

[75] Inventors: Peter Haas, Haan; Claus-Dieter Sommerfeld, Much; Hans-Ulrich Weber, Monheim, all of Fed. Rep. of Germany

[73] Assignee: Bayer Aktiengesellschaft, Bayerwerk, Fed. Rep. of Germany

[21] Appl. No.: 914,110

[22] Filed: Oct. 1, 1986

[30] Foreign Application Priority Data

Oct. 8, 1985 [DE] Fed. Rep. of Germany ....... 3535861
Mar. 18, 1986 [DE] Fed. Rep. of Germany ....... 3608962

[51] Int. Cl.$^4$ ...................... C08G 18/00; C08G 18/14; C08G 18/32
[52] U.S. Cl. ...................... 521/167; 528/77; 564/59
[58] Field of Search ........................ 521/167; 528/77; 564/59

[56] References Cited

U.S. PATENT DOCUMENTS

| | | | |
|---|---|---|---|
| 3,277,027 | 10/1966 | Hennig et al. | 528/77 |
| 3,277,061 | 10/1966 | Fenton | 564/59 |
| 3,321,415 | 5/1967 | Hennig et al. | 528/77 |
| 3,519,680 | 7/1970 | Wismer et al. | 560/160 |
| 3,795,638 | 3/1974 | Grogler et al. | 524/213 |
| 4,180,131 | 12/1979 | Chammas | 166/55 |
| 4,546,121 | 10/1985 | Haas et al. | 521/164 |

FOREIGN PATENT DOCUMENTS

| | | | |
|---|---|---|---|
| 2106726 | 8/1972 | Fed. Rep. of Germany. | |
| 2349278 | 4/1975 | Fed. Rep. of Germany. | |
| 3015374 | 10/1981 | Fed. Rep. of Germany. | |
| 947847 | 6/1947 | France. | |
| 2360619 | 2/1978 | France. | |
| 2381077 | 10/1978 | France. | |
| 1037376 | 7/1966 | United Kingdom | 521/167 |
| 1561187 | 2/1980 | United Kingdom. | |

*Primary Examiner*—John Kight
*Assistant Examiner*—Dennis R. Daley
*Attorney, Agent, or Firm*—Gene Harsh; Joseph C. Gil; Thomas W. Roy

[57] ABSTRACT

The present invention is directed to novel polyhydroxyalkyl oligoureas prepared by condensing urea derivatives with polyamides. The present invention is further directed to polyether polyols prepared by alkoxylating these polyhydroxyalkyl oligoureas. Finally, the present invention is directed to the use of both the polyhydroxyalkyl oligoureas and the polyethers prepared therefrom for use in the production of polyurethanes, particularly rigid foams.

15 Claims, No Drawings

OLIGOUREA POLYOLS, POLYETHER POLYOLS PRODUCED FROM THEM AND THE USE OF THESE POLYOLS IN THE ISOCYANATE POLYADDITION PROCESS

BACKGROUND OF THE INVENTION

1. Field of the Invention

The present invention is directed to polyhydroxyalkyl oligoureas, polyether polyols obtained by alkoxylating the polyhydroxy alkyl oligoureas and the use of both of these products for the production of isocyanate polyaddition products, particularly rigid foams.

2. Description of the Prior Art

A variety of starter molecules have previously been described for the production of polyols for the isocyanate polyaddition process, depending upon the desired functionality. The properties and molecular weight thereof are then adjusted by the addition of predominantly oxirane derivatives.

Starts for these polyols include diols, triols, like glycerine, trimethylolpropane, pentaerythritol, sucrose or glucose. However, urea has also been used as a starting molecule as described, for example, in FR-P Nos. 7,700,831, 7,624,154, 947,847, BE-P No. 678,064 and U.S. Pat. No. 4,180,131. In comparison with high functionality starters, urea has the disadvantage of having a low functionality which is generally about 2.

Hydroxyalkyl mono ureas have been described as incorporabel flame-proofing agents for polyurethane integral foams in the German Offenlegungsschrift No. 3,332,794.

SUMMARY OF THE INVENTION

The present invention relates to novel polyhydroxyalkyl oligoureas corresponding the formula I $$\text{HO-}(CR_2^2)_n\diagdown\text{N-}\overset{O}{\underset{\|}{C}}\text{-}\overset{R^1}{\underset{|}{N}}\text{-}(CR_2^2)_m\text{-}\left[\text{N-}(CR_2^2)_m\right]_o\text{-}\overset{R^1}{\underset{|}{N}}\text{-}\overset{O}{\underset{\|}{C}}\text{-N}\diagup(CR_2^2)_n\text{-OH} \quad (I)$$

with the internal branch bearing $C=O$ and $N(CR_2^2)_n$-OH / $(CR_2^2)_n$-OH groups.

in which
the radicals $R^1$, the same or different, represent hydrogen or a $C_1$-$C_4$-alkyl radical, preferably a methyl radical or hydrogen and, if o is equal to zero, two groups $R^1$ together can also represent a $C_1$-$C_6$-alkylene, preferably a $C_1$-$C_3$-alkylene, more preferably a $C_2$-$C_3$-alkylene and most preferably a $C_2$-alkylene radical, in which case m has to be equal to 2 or 3, the radicals $R^2$, the same or different, represent hydrogen or a $C_1$-$C_4$-alkyl radical, preferably a methyl radical or hydrogen,
n is an integer from 2 to 6
m is an integer from 2 to 10
o is an integer from 0 to 6, preferably from 0 to 3, most preferably 0 or 1 or formula II $$N\text{-}\!\left[(CR_2^2)_m\text{-}\overset{R^1}{\underset{|}{N}}\text{-}\overset{O}{\underset{\|}{C}}\text{-N}\diagup_{\diagdown}{(CR_2^2)_n\text{-OH} \atop (CR_2^2)_n\text{-OH}}\right]_3 \quad (II)$$

in which
the radicals $R^1$ represents hydrogen or a $C_1$-$C_4$-alkyl radical, preferably a methyl radical or hydrogen,
the radicals $R^2$, the same or different, represent hydrogen or a $C_1$-$C_4$-alkyl radical, preferably a methyl radical or hydrogen,
n is an integer from 2 to 6 and
m is an integer from 2 to 10.

The groups $(CR^2)_n$ preferably represent —($CH_2$—$CH_2$)— and/or $$-(\underset{\underset{CH_3}{|}}{CH}-CH_2)-\text{groups.}$$

The invention also relates to polyether polyols obtainable by alkoxylation of the above mentioned polyhydroxyalkyl oligoureas of formula I or II.

The invention further relates to the use of polyhydroxyalkyl-oligoureas and polyether polyols obtainable therefrom as a reaction component in the isocyanate polyaddition process for the production of polyurethanes, preferably of rigid foams based on polyurethanes or polyisocyanurates.

DETAILED DESCRIPTION OF THE INVENTION

Compounds of formulas I and II in which:
n is equal to 2 or 3
m is equal to 2 or 3
o is equal to 0 or 3, most preferably is equal to 0 or 1,
$R^1$, $R^2$ represent hydrogen in the general formulas are preferred.

Polyether polyols obtainable by alkoxylation of the polyhydroxyalkyl oligoureas with ethylene oxide and/or propylene oxide are preferred according to the invention. The polyether polyols have an OH number of about 25 to 700.

The polyhydroxyalkyl oligoureas according to the invention are produced, for example, by condensation of urea derivatives having the structure (III)

$$NH_2\text{-}\overset{O}{\underset{\|}{C}}\text{-N}\diagup_{\diagdown}{(CR_2^2)_n\text{-OH} \atop (CR_2^2)_n\text{-OH}} \quad (III)$$

with amines having the structure IV and V

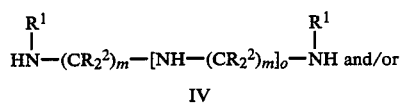

IV

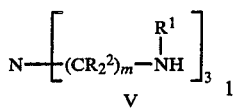

V wherein:

n, m, $R^1$, $R^2$ and o have the meaning given above, with formation of ammonia.

These high functionality starters can be adjusted to any molecular weight or hydroxyl number by alkoxylation with oxirane derivatives such as ethylene oxide, propylene oxide, butylene oxide or epichlorohydrin.

A further advantage of the oligoureas according to the invention resides in the fact that these hydroxyalkyl ureas can be alkoxylated not only at the hydroxy groups, but also at the urea hydrogen atom as this group can be acylated and alkoxylated smoothly.

Starting materials for the production of the hydroxyalkyl oligoureas according to the invention include aliphatic or cycloaliphatic diamines such as imidazolidine, 1,3-diazacycloheptane, piperazine, ethylene diamine, 1,2-propylene diamine, 1,4-diamino butane, 1,5-diamino pentane, 1,6-diamino hexane, 1,8-diamino octaine, 1,10-diaminodecane, 1,4-diaminocyclohexane, isophorone diamine and 4,4'- and/or 2,4'- and/or 2,2'-diamino dicyclohexylmethane as well as $C_1$–$C_4$ mono- to tetraalkyl derivatives thereof; polyamines such as diethylene triamine, triethylene tetramine, tetraethylene pentamine, pentaethylene hexamine and hexaethylene heptamine; and tertiary amino group containing polyamines such as tris-(3-amino-n-propyl)-amine, tris-(2-aminoethyl)-amine, tris-(4-amino-n-butyl)-amine, or tris (2-amino-2-methyl-ethyl)-amine.

The N,N-bis-hydroxyalkyl ureas of formula (III), are produced, for example, by condensation of urea with bis-hydroxyalkyl amines with expulsion of ammonia. Condensation may also be carried out in a single stage process so that urea, bis-hydroxyalkylamines as well as the di- and polyamines are condensed directly.

Examples of the polyhydroxyalkyl oligoureas according to the invention include:

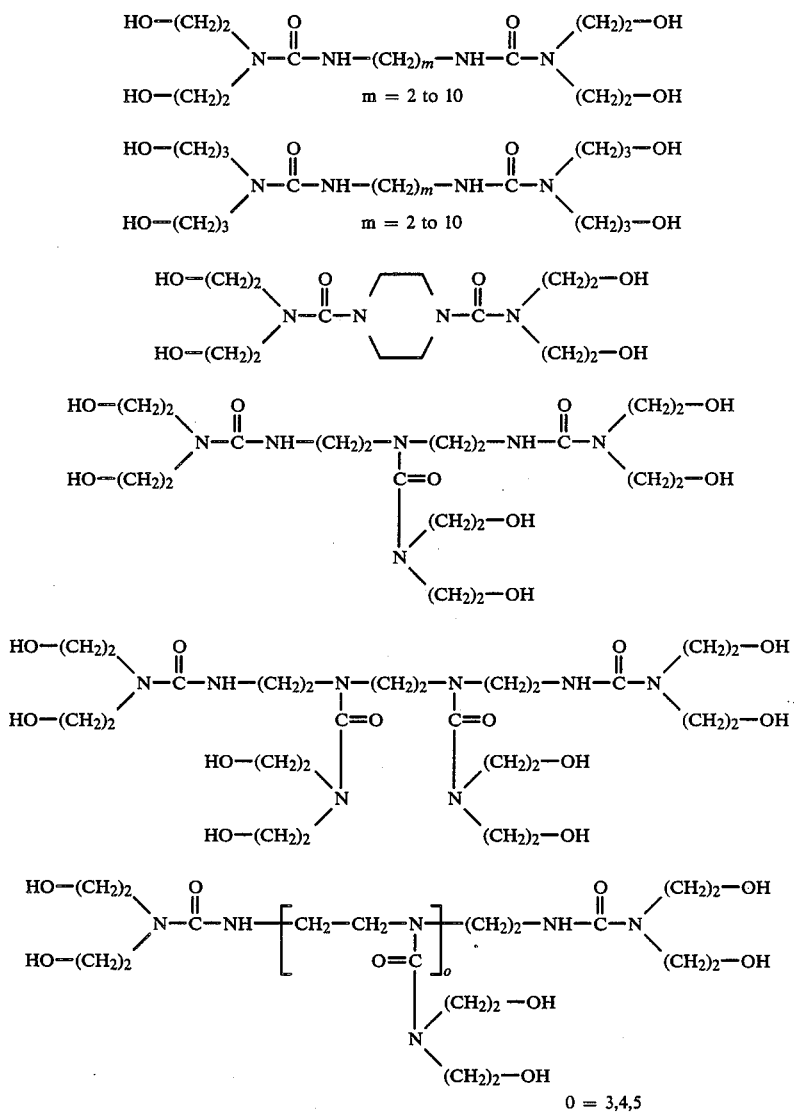

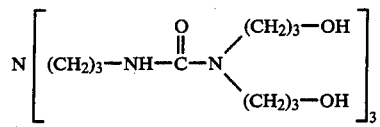

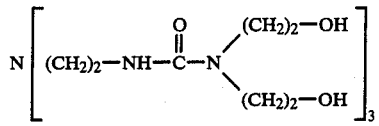

The polyhydroxyalkyl oligoureas I and/or II according to the invention are generally reacted under normal conditions with oxirane derivatives, preferably ethylene oxide and/or propylele oxide. When mixtures of oxiranes are used, they may be reacted as mixtures or sequentially. Polyether polyols having hydroxyl numbers of about 25 to 700, preferably about 250 to 600 are obtained. However, the polyhydroxyalkyl oligoureas can also be used without alkoxylation as a reaction component in the isocyanate polyaddition process.

The polyhydroxyalkyl oligoureas according to the invention and the alkoxylation products thereof (polyether polyols) impart new properties to foam reactive systems and/or polyurethane foams, preferably polyurethane rigid foams, such as:

- self-catalysis, so that activators can be dispensed within the reactive system,
- high foam stability in the forming foam so that stabilizers can be dispensed with
- extremely fine cells in the foam even without cell regulators or emulsifiers,
- cold deformability and
- thermoplastic properties, i.e. they produce, for example, thermoplastically deformable rigid foams, so that they represent valuable polyol components in the context of the isocyanate polyaddition reaction. Polyisocyanurate foams may also be produced with the polyols according to the invention.

In order to produce rigid foams, preferably polyurethane (urea) and/or polyisocyanurate rigid foams, the following substances are used in addition to the polyols according to the invention:

1. aliphatic, cycloaliphatic, araliphatic, heterocyclic and, in particular, aromatic di- and/or polyisocyanates of the type described, for example, by W. Siefken in Justus Liebigs Annalen der Chemie, 562, pages 75 to 136 (1949). Examples include those corresponding to the formula $Q(NCO)_n$, in which $n=2$ to 4, preferably 2, and Q represents an aliphatic hydrocarbon radical containing 2 to 18, preferably 6 to 12 carbon atoms; a cycloaliphatic hydrocarbon radical containing 4 to 20, preferably 5 to 11 carbon atoms; an aromatic hydrocarbon radical containing 6 to 20, preferably 6 to 13 carbon atoms; or an araliphatic hydrocarbon radical containing 8 to 15, preferably 8 to 13 carbon atoms, for example, polyisocyanates of the type described in DE-A No. 2,832,253 at pages 10 to 11 (U.S. Pat. No. 4,263,408, herein incorporated by reference in its entirety, at columns 3 and 4). The polyisocyanates which are obtainable commercially, for example 2,4- and/or 2,6-toluylene diisocyanate as well as any mixtures of these isomers ("TDI"), diphenylmethanediisocyanates (4,4'- and/or 2,4'- and/or 2,2'-isomers), polyphenyl-polymethylene-polyisocyanates of the type produced by aniline formaldehyde condensation and subsequent phosgenation ("crude MDI") and "modified polyisocyanates", which contain, for example, carbodiimide groups, urethane groups, allophanate groups, isocyanurate groups, urea groups and/or biuret groups, in particular those modified polyisocyanates derived from 2,4- and/or 2,6-toluylene diisocyanate and preferably from 4,4'- and/or 2,4'-diphenylmethane diisocyanate are particularly preferred.

When the isocyanate-reactive compounds are difunctional, then modified polyisocyanates having a functionality higher than 2.0 and trifunctional and/or higher functional polyisocyanates are preferably used.

2. Compounds containing at least two hydrogen atoms which are reactive towards isocyanates and have a molecular weight of 18 to 399 may optionally be used as starting materials for the production of polyurethanes. These include compounds containing hydroxyl groups, amino groups, thiol groups, carboxyl groups and/or hydrazide groups, preferably compounds containing hydroxyl groups and/or amino groups, which act as chain extenders or cross-linking agents. These compounds generally contain 2 to 8, preferably 2 to 4 hydrogen atoms which are reactive towards isocyanates. Examples are described in DE-A No. 2,832,253 at pages 19 to 20, U.S. Pat. No. 4,236,408 at column 7. Water, hydrazine, ethylene glycol, butane-1,4-diol, trimethylolpropane, formitol mixtures or adipic acid dihydrazide are included.

3. Compounds containing at least two hydrogen atoms which are reactive towards isocyanates and have a molecular weight of 400 to about 10,000, preferably about 600 to 6000 and most preferably 1500 to 4000, may optionally be used in combination with the polyurea polyols according to the invention. In addition to compounds containing amino groups, thio groups or carboxyl grops, preferred compounds include those containing hydroxyl groups, in particular compounds containing from 2 to 8, preferably 2 to 4 hydroxyl groups, such as polyesters, polyethers, polythioethers, polyacetals, polycarbonates and polyester amides of the type known for the production of homogeneous and cellulse polyurethanes and described, for example, in DE-A No. 2,832,253 at pages 11 to 18, (U.S. Pat. No. 4,263,408 at columns 4–7). Polyethers obtained by addition of one or more alkylene oxides (ethylene oxide and, in particular, propylene oxide) to divalent or polyvalent "starters" (propylene glycol, glycerine, sorbitol, formose, triethanolamine, trimethylol propane) are particularly preferred, as well as polyethers which contain dispersed or dissolved polyaddition products of diisocyanates and hydrazine, diamines and/or glycols or polymers and/or graft polymers, preferably of styrene and acrylonitrile. The preferred polyethers have an average functionality above 2.0.

4. Auxiliaries and additives such as readily volatile inorganic, but preferably organic substances which may optionally be used as blowing agents; catalysts of the type known per se such as tertiary amines and tin(II)- and tin(VI)- compounds; surface active additives such as emulsifiers and foam stabilizers; reaction retarders, for example, acidic substances such as hydrochloric acid or organic acid halides; cell regulators such as paraffins, fatty alcohols or dimethyl polysiloxanes; pigments or dyes; stabilizers against the influences of aging, light and weathering; plasticizers; fungistatically- and bacteriostatically-acting substances; and fillers. These auxiliaries and additives which may be used are described in detail, for example, in DE-A No. 2,732,292 at pages 21 to 24, (U.S. Pat. No. 4,248,930, herein incorporated by reference in its entirety, at columns 8-10). Further examples of the auxiliaries and additives are described in Kunststoff-Handbuch, volume VII, edited by Vieweg and Hochtlen, Carl-Hanser-Verlag, Munich 1966 on pages 103 to 113 in Kunststoff-Handbuch, volume VII, edited by Becker and Braun, Carl-Hanser-Verlag, Munich 1983 on pages 92 to 111.

Rigid foams produced using the polyurea polyols according to the invention may be used as insulating panels, sandwich elements with various surface layers, in situ foams such as injection-molded foam or rigid foams produced by the overlay process, solar panel fillings, pipe insulation, filling and assembly foams and block foams.

They are produced by continuous or batch-wise processes for the processing of polyurethanes such as laminator methods, injection or casting processes, with high pressure or low pressure foaming machinery.

The invention is further illustrated, but is not intended to be limited by the following examples in which all parts and percentages are by weight unless otherwise specified.

EXAMPLES

EXAMPLE 1

$$NH_2-\overset{\overset{O}{\|}}{C}-N(CH_2-CH_2-OH)_2$$

(a) The above compound was prepared from 1200 g (20 mol) of urea and 2100 g (20 mol) of diethanolamine by explusion of ammonia at 100° to 120° C. with aftertreatment in a water jet vacuum; the reaction product solidified on cooling.

Quantitative yield, OH number 766 (calculated 750).

$$(HO-CH_2-CH_2)_2N-\overset{\overset{O}{\|}}{C}-NH-CH_2-CH_2-NH-\overset{\overset{O}{\|}}{C}-N(CH_2-CH_2-OH)_2$$

(b) The above compound was prepared from 592 g (4 mol) of the compound obtained according to a) and 120 g (2 mol) of ethylene diamine by heating to 130° C. with elimination of ammonia and subsequent treatment in a water jet vacuum.

Yield: 630 g, almost quantitative.
Viscosity: 5800 mPa.s (25° C.).
OH number calculated for tetrafunctionality 695 (OH groups only),
OH number* calculated for hexafunctionality 1040 (OH groups plus NH groups from the urea group),
OH number* found 970,

*  NH groups from the urea group are included by acylation when determining the OH number.

EXAMPLE 2

$$(HO-CH_2-CH_2)_2N-\overset{\overset{O}{\|}}{C}-NH-CH_2-CH_2-\underset{\underset{\underset{N(CH_2-CH_2-OH)_2}{|}}{\overset{|}{C=O}}}{N}-CH_2-CH_2-NH-\overset{\overset{O}{\|}}{C}-N(CH_2-CH_2-OH)_2$$

The above compound was prepared from 1776 g (12 mol) of the compound a) of Example 1 and 412 g (4 mol) of diethylene triamine by explusion of ammonia at 120° to 140° C. with subsequent treatment under vacuum.

Yield: 1975 g, almost quantitative,
OH number calculated for hexafunctionality 675,
OH number* calculated for octafunctionality 902,
OH number* found 900,
Viscosity 19,500 mPa.s (25° C.).

EXAMPLE 3

180 g (3 mol) of urea, 315 g (3 mol) of diethanol amine and 103 g (1 mol) of diethylene triamine were heated to a temperature of from 110° to 135° C. After about 10 hours the mixture was cooled to 80° C. and a water jet vacuum was applied.

Yield: 494.5 (quantitative),
Viscosity 28,000 mPa.s (25° C.),
OH number: 800.

EXAMPLE 4

$$(HO-\overset{\overset{CH_3}{|}}{CH}-CH_2)_2N-\overset{\overset{O}{\|}}{C}-NH_2$$

(a) The above compound was prepared from 332.5 g (2.5 mol) of diisopropanolamine and 150 g (2.5 mol) of urea by explusion of ammonia at 120° C. and subsequent treatment under vacuum.

Yield: quantitative,
OH number 640 (calculated 636),
* see explanation of Example 1.

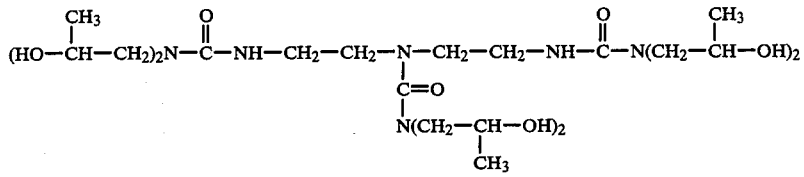

(b) The above compound was prepared from 264 g (1.5 mol) of the compound according to (a) and 51.5 g (0.5 mol) of diethylene triamine by heating to 130° C. and expulsion of ammonia as well as subsequent treatment under vacuum.

Yield: quantitative,
OH number calculated for octafunctionality 770,
OH number found 750,
Viscosity 47,500 mPa.s (25° C.).

EXAMPLE 5

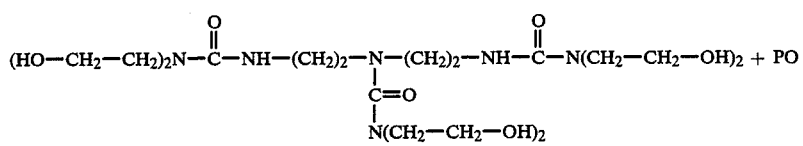

2059 g of the compound according to Example 2 were reacted with 67 g of 45% KOH and subsequently 32 g of water were distilled off, and subsequently 3941 g of propylene oxide were applied under pressure at 100° C. within 12 hours. The mixtures was neutralized with 26.4 g of sulphuric acid in 600 g of water, concentrated and suction filtered.

Yield: 5420 g,
OH number: 386,
Viscosity: 1200 mPa.s (25° C.).

EXAMPLE 6

20.6 kg of the compound according to Example 2 were reacted with 670 g of 45% KOH and then water was distilled off. Afterwards, 21.65 kg of propylene oxide were applied under pressure at 110° C. within 13 hours. The mixture was neutralized with 264 g of sulphuric acid in 6000 g of water, concentrated and suction filtered.

Yield: 40.3 kg
OH number: 439
Viscosity 2175 mPa.s (25° C.)
Water content 0.05%.

EXAMPLE 7

2060 g of the compound according to Example (1b) were reacted with 67 g of 45% KOH concentrated and then reacted with 1810 g of propylene oxide at 110° C. within 10 hours. The mixture was neutralized with 26.4 g of sulphuric acid in 700 g of water, concentrated and suction filtered.

Yield: 3.8 kg, OH number 395.

EXAMPLE 8

98 g of the polyether polyol produced according to Example 6, 1.5 g of water, 2.0 g of a foam stabilizer according to DE-OS No. 2,029,293 Stabilizer OS 720 ® of Bayer AG and 39 g of trifluoromonochloromethane as a blowing agent were mixed.

This mixture was foamed with 133 g of polymeric 4.4'-diisocyanato di phenylmethane (NCO content of 31%) having an average functionality of 2,7(MONDUR MR ®). A fine-celled rigid foam which was free from amino odor and had a very smooth surface was formed due to the self-catalytic effect of the polyether polyol according to the invention. Due to the poor air dissolving capacity, the foam did not have "worm holes".

The foam obtained had the following physical data:
Setting time: 75 seconds.
Bulk density: 20 kg/m$^3$ (free foam),
Bulk density: 31.5 kg/m$^3$ (shaped foam),
Pressure-resistance: 0.11 MPa (for bulk density of 31.5 kg/m$^3$).

EXAMPLE 9

98.5 g of the polyether polyol produced according to Example 6, 1.5 g of water and 39 g of trifluoromonochloromethane were mixed. This mixture was foamed with 133 g of crude 4,4'-diisocyanatodiphenylmethane (NCO content 31%) as set forth in example 8.

A tough rigid foam having a fine, surprisingly uniform cell structure, produced without foam stabilizer and activator, was formed.
Physical data:
Setting time: 70 seconds,
Bulk density: 21 kg/m$^3$.

EXAMPLE 10

68.5 g of the polyether polyol produced according to Example 6, 29.6 g of a polyether polyol (obtained by the addition of propylene oxide to a mixture of sucrose, propylene glycol, and water in the weight ratio of 75:15:10 and having an OH number of 470), 1.9 g of water, 0.2 g of a foam stabilizer according to example 8, 0.9 g of dimethylcyclohexylamine and 36 g of trifluoromonochloromethane were mixed.

This mixture was foamed with 144 g of polymeric 4,4'-diisocyanato diphenylmethane (NCO content 31%) as set forth in example 8. A freely flowing raw material mixture as well as a fine-celled rigid foam having a very smooth surface were formed.
Physical data:
Setting time: 75 seconds,
Bulk density: 21 kg/m$^3$ (free foam),
Bulk density: 32 kg/m$^3$ (shaped foam),
Pressure resistance: 0.11 MPa (when bulk density is 32 kg/m$^3$).

EXAMPLE 11

96.5 g of the polyether polyol produced according to Example 6, 1.5 g of water, 2 g of a foam stabilizer according to DE-OS No. 2,092,293, 0.5 g of N,N,N',N'',N''-pentamethyldiethylene triamine, 5 g of a 98:2 mixture of dimethylcyclohexylamine and dibutyl tin dilaurate and 39 g of trifluoromonochloromethane were mixed.

This mixture was mixed with 133 g of polymeric 4,4'-diisocyantodiphenylmethane (NCO content 31%) as set forth in Example 8 and was then injected. The injection moled rigid foam was very fine-celled and exhibited good layer adhesion as well as a smooth surface.

Physical data:
Setting time: 10 seconds,
Bulk density: 35 kg/cm$^3$,
Pressure resistance: 0.19 MPa,
Proportion of open cells: (according to ASTM-D-1940) 7% by volume,
Transverse tensile test: (strength) 0.4 MPa.

EXAMPLE 12

98 g of the polyether polyol produced according to Example 5, 1 g of foam stabilizer according to Example 8, 1 g of a 25% solution of potassium acette in diethylene glycol and 40 g of trifluoromonochloromethane were mixed.

This mixture was foamed with 198 g of crude 4,4'-diisocyanatodiphenylmethane (NC-content 31%) A fine-celled rigid polyisocyanurate foam was formed.

Physical data:
Setting time: 80 seconds,
Bulk density: 35 kg/cm$^3$ (free foam).

EXAMPLE 13

98 g of the polyether polyol produced according to Example 6, 1 g of a foam stabilizer according to Example 8, 1 g of a solution of potassium acetate in diethyleneglycol, 15 g of a tris-β-chloroethyl phosphonate and 40 g of trifluoromonochloromethane were mixed.

This mixture was foamed with 206 g of polymeric 4,4'-diisocyanatodiphenylmethane (NCO content 31%) as set forth in Example 8. A fine-celled, flame-resistant polyisocyanurate foam was formed.

Physical data:
Setting Time: 90 seconds,
Bulk density: 40 kg/cm$^3$ (free foam),
Bulk density: 43 kg/cm$^3$ (shaped foam),
Pressure resistance: 0.26 MPa (when bulk density is 43 kg/m$^3$),
Proportion of open cells: (according to ASTM-D-1940) 8% by volume.

EXAMPLE 14

30 g of the polyether polyol according to Example 6, 35 g of a polyester polyol having a hydroxyl number 200 (obtained by reacting a 80:20 mixture of phthalic acid anhydride and adipic acid with diethylene glycol), 30 g of a polyether polyol having a hydroxyl number of 180 (obtained by the addition of ethylene oxide to propylene glycol), 2.8 g of water and 0.3 g of a foam stabilizer according to Example 8 were mixed.

This mixture was foamed with 150 g of polymeric 4,4'-diisocyanato diphenylmethane (NCO-content 31%) as set forth in Example 8. A tough, fine-celled rigid foam which was thermoplastically processible was formed.

Physical data:
Setting time: 80 seconds,
Bulk density: 45 kg/cm$^3$ (free foam),
Heating time (at 170° C.): 3 minutes to thermoplastic deformation.

EXAMPLE 15

57.6 g of a polyether polyol of hydroxyl number 380 (obtained by addition of propylene oxide to a mixture of sucrose, propylene glycol and water), 28.8 g of the polyether polyol produced according to Example 6, 9.6 g of a polyester polyol (obtained by the addition of propylene oxides to ethylene diamine) and having an OH number of 650, 2 g of water, 2 g of a foam stabilizer according to Examples 8, 1.7 g of dimethylcyclohexylamine and 35 g of trifluoromonochloromethane were mixed.

This mixture was foamed with 136 g of polymeric 4,4'-diisocyanatodiphenylmethane (NCO content 31%) as set forth in Example 8. A very fine-celled rigid foam having a very smooth surface was formed.

Physical data:
Setting time: 80 seconds,
Bulk density: 21 kg/cm$^3$ (free foam).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyhydroxyalkyl oligourea corresponding to formula I $$\begin{array}{c} HO-(CR_2^2)_n \\ \phantom{HO-(CR_2^2)_n} \diagdown \\ HO-(CR_2^2)_n \end{array} N-\overset{\overset{O}{\|}}{C}-\overset{\overset{R^1}{|}}{N}-(CR_2^2)_m-$$

$$\left[\begin{array}{c} N-(CR_2^2)_m- \\ | \\ C=O \\ | \\ N \diagup (CR_2^2)_n-OH \\ \phantom{N} \diagdown (CR_2^2)_n-OH \end{array}\right]_o \overset{\overset{R^1}{|}}{N}-\overset{\overset{O}{\|}}{C}-N\diagup\phantom{(}(CR_2^2)_n-OH \\ \phantom{\overset{\overset{R^1}{|}}{N}-\overset{\overset{O}{\|}}{C}-N}\diagdown(CR_2^2)_n-OH$$

or corresponding to formula II $$N-\left[-(CR_2^2)_m-\overset{\overset{R^1}{|}}{N}-\overset{\overset{}{\underset{\|}{C}}}{\underset{O}{}}-N\diagup\phantom{(}(CR_2^2)_n-OH \diagdown (CR_2^2)_n-OH\right]_3$$

wherein
the radicals R$^1$, which may be the same or different, represent hydrogen or a C$_1$–C$_4$-alkyl radical, provided that when o is equal to zero the radicals R$^1$ cannot represent hydrogen, but can form together a C$_2$–C$_5$-alkylene radical, in which case m is 2 or 3,
the radicals R$^2$, which may be the same or different, represent hydrogen or a C$_1$–C$_4$-alkyl radical,
n is an integer from 2 to 6,
m is an integer from 2 to 10 and
o is an integer from 0 to 6.

2. The polyhydroxyalkyl oligourea of claim 1 wherein n is equal to 2 or 3,
m is equal to 2 or 3,
$R^1$ and $R^2$ represent hydrogen and
o is an integer from 1 to 5.

3. A polyether polyol obtained by the alkoxylation of the polyhydroxyalkyl oligourea corresponding to formula I

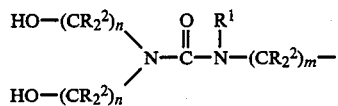

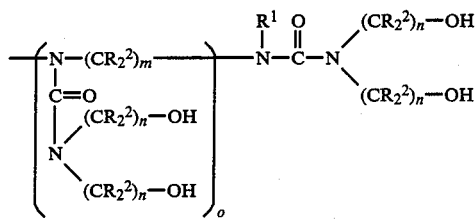

or corresponding to formula II

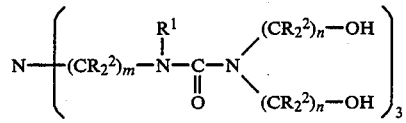

wherein
the radicals $R^1$, which may be the same or different, represent hydrogen or a $C_1$–$C_4$-alkyl radical, provided that when o is equal to zero the radicals $R^1$ can form together a $C_2$–$C_5$-alkylene radical, in which case m is 2 or 3,
the radicals $R^2$, which may be the same or different, represent hydrogen or a $C_1$–$C_4$-alkyl radical,
n is an integer from 2 to 6,
m is an integer from 2 to 10 and
o is an integer from 0 to 6.

4. The polyether polyol of claim 3 wherein
n is equal to 2 or 3,
m is equal to 2 or 3 and
$R^1$ and $R^2$ represent hydrogen.

5. The polyether polyol of claim 3 wherein said alkoxylation is conducted with ethylene oxide and/or propylene oxide.

6. The polyether polyol of claim 4 wherein said alkoxylation is conducted with ethylene oxide and/or propylene oxide.

7. The polyether polyol of claim 3 wherein said polyether polyol has an OH number of about 25 to 700.

8. The polyether polyol of claim 4 wherein said polyether polyol has an OH number of about 25 to 700.

9. The polyether polyol of claim 5 wherein said polyether polyol has an OH number of about 25 to 700.

10. The polyether polyol of claim 6 wherein said polyether polyol has an OH number of about 25 to 700.

11. A process for the production of a polyurethane which comprises reacting a polyisocyanate with a polyol component comprising the polyhydroxy alkyl oligourea of claim 1.

12. A process for the production of a polyurethane which comprises reacting a polyisocyanate with a polyol component comprising the polyether polyol of claim 3.

13. The process of claim 11 wherein said polyurethane is a polyurethane rigid foam.

14. The process of claim 12 wherein said polyurethane is a polyurethane rigid foam.

15. The polyhydroxyalkyl oligourea of claim 2 wherein o is equal to 1.

* * * * *